United States Patent [19]

Goldberger

[11] Patent Number: 4,909,252
[45] Date of Patent: Mar. 20, 1990

[54] PERFUSION BALLOON CATHETER

[75] Inventor: Jeffrey Goldberger, San Francisco, Calif.

[73] Assignee: The Regents of the Univ. of California, Oakland, Calif.

[21] Appl. No.: 199,128

[22] Filed: May 26, 1988

[51] Int. Cl.$^4$ .............................................. A61M 29/02
[52] U.S. Cl. ......................................... 606/194; 604/96
[58] Field of Search .................................. 604/96–103; 128/325, 344, 348.1

[56] References Cited

U.S. PATENT DOCUMENTS

| | | | |
|---|---|---|---|
| 2,548,602 | 4/1951 | Greenberg | 604/96 X |
| 2,883,986 | 4/1959 | DeLuca | 604/96 X |
| 4,183,102 | 1/1980 | Guiset | 604/101 X |
| 4,198,981 | 4/1980 | Sinnreich | 604/101 X |
| 4,289,128 | 9/1981 | Rüsch | 128/207.15 |
| 4,581,017 | 4/1986 | Sahota | 604/101 |
| 4,641,653 | 2/1987 | Rockey | 604/96 X |
| 4,692,200 | 9/1987 | Powell | 128/344 X |
| 4,762,129 | 8/1988 | Bonzel | 128/344 |

FOREIGN PATENT DOCUMENTS 8800071  1/1988  World Int. Prop. O. .......... 128/344

Primary Examiner—Dalton L. Truluck
Attorney, Agent, or Firm—Majestic, Parsons, Siebert & Hsue

[57] ABSTRACT

A balloon catheter utilizing a perfusion balloon at one end thereof is described. The perfusion balloon has a donut shaped cross section having a central opening formed therethrough. The central opening provides a blood flow passage even when the balloon is fully inflated. When inflated, the perfusion balloon is used to dilate a stenotic region of a blood vessel or heart valve to restore blood flow. After deflation, if the blood vessel collapses, the balloon catheter of the present invention can be reinflated and kept in place while the patient is prepared for surgery. In this manner, acceptable blood flow is provided regardless of the length of time required for surgical preparation. In an alternate embodiment, a one-way valve is formed integrally with the perfusion balloon so that the present invention may be better applied to valvuloplasty. In this application, the balloon is inflated at a stenotic region of a heart valve to expand the valve and restore acceptable blood flow. The one-way valve of the perfusion balloon takes the place of the coronary valve so that normal operation of the heart can be maintained during the valvuloplasty process.

19 Claims, 2 Drawing Sheets

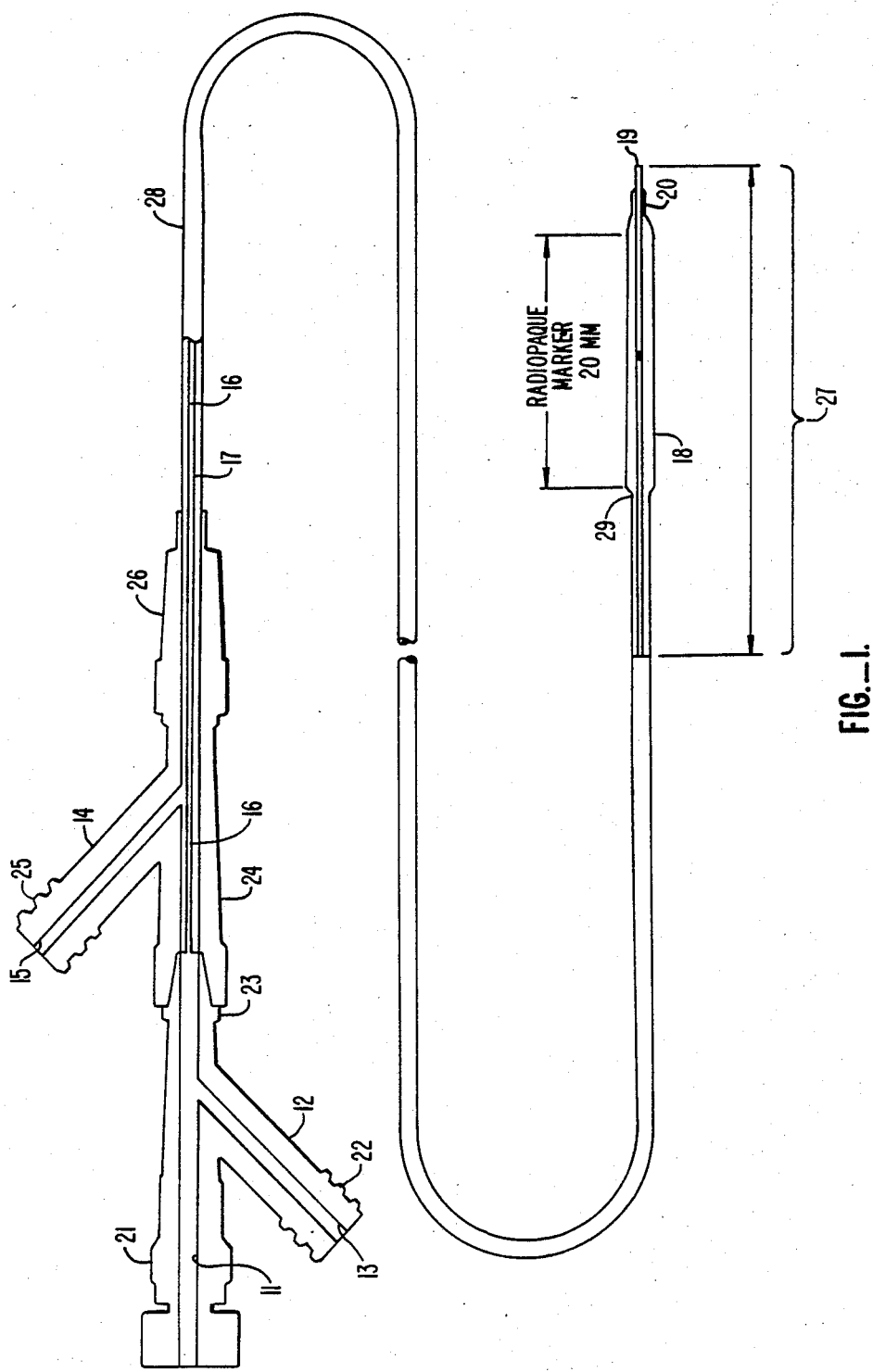
FIG._1.

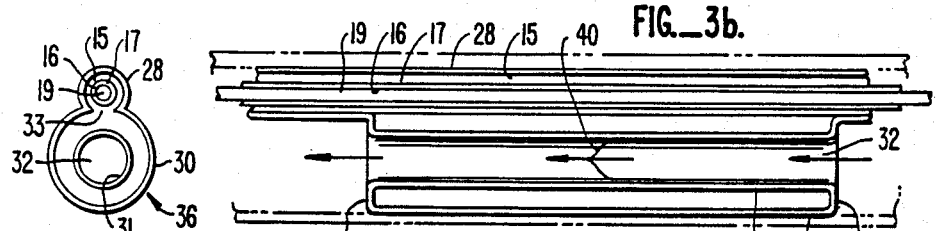
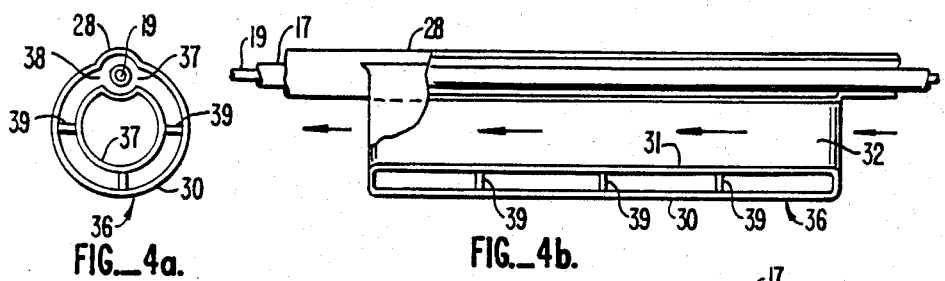
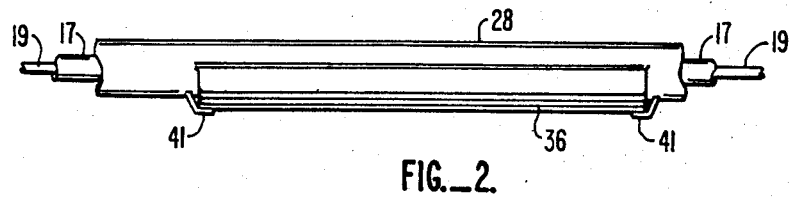
FIG._2.

PERFUSION BALLOON CATHETER

BACKGROUND OF THE PRESENT INVENTION

1. Field of the Invention

This invention relates to the field of catheters and in particular to coronary dilation catheter assemblies utilizing a perfusion balloon at one end thereof.

2. Background Art

A blood vessel of a circulatory system can often become narrow to the point where the flow of blood is limited or severely restricted. This narrowing of the blood vessel region is called a "stenosis" and is caused by the growth or development of a mass or lesion on the inner walls of the blood vesse. The stenosis must be removed, compressed, or bypassed to restore maximum blood flow capability to the blood vessel. Presently, the methods for treating stenosis of a blood vessel comprise either a surgical procedure or angioplasty.

The method known as angioplasty involves the insertion of a balloon catheter into a blood vessel at the stenotic region. The balloon is then inflated to compress the lesion material comprising the stenosis back against the walls of the blood vessel and ideally, permanently compressing the lesion material to increase the diameter of the blood vessel and hence blood flow rate of the blood vessel.

Prior art angioplasty catheters comprise a guide wire designed as either part of an angioplasty catheter or to fit inside one which is inserted through a guiding catheter into the circulatory system at some location and advanced through the blood vessel to a point past the stenosis. A balloon catheter comprising a balloon fastened around the exterior of a hollow catheter tube is inserted about the wire and slid over the guide wire until it is at the point of the stenosis.

Once in place, the balloon is inflated with a suitable fluid to dilate the lesion causing the stenosis. The balloon is then deflated and the stenotic region is observed to see if blood flow is restored. This may involved completely removing the catheter assembly and measuring the rate of blood flow through the blood vessel. If the stenosis is not compressed and springs back into place, closing the vessel, or if the blood vessel completely collapses, the patient may need to undergo surgery if the blood vessel cannot be maintained open by further dilatations. This must be done as soon as possible because a blood vessel cannot be blocked for more than a short period of time without damaging the tissue that it supplies. Therefore, while the catheter procedure can often prevent the need for surgery, it is still necessary to have the surgeons and operating room on standby during the procedure, tus incurring the expense of preparing completely for surgery during the procedure.

One disadvantage of such prior art balloon catheters is the complete occlusion of the vessel during the angioplasty process. Typically, the balloon can only remain inflated for a few secons before it must be deflated to permit blood flow to continue. Further, the catheter often must be completely removed from the blood vessel to determine if the procedure was successful.

Therefore, it is desirable to provide an angioplasty catheter in which a blood flow path is provided past the stenotic region of a blood vessel receiving the angioplasty treatment. It is also desirable to provide a catheter assembly which can be left in place while the effectiveness of treatment is determined. One prior art attempt to provide such a catheter is described in U.S. Pat. No. 4,581,017 to Sahota. There, small orifices are provided in the proximal end of the balloon catheter adjacent to the balloon and at the distal end of the catheter adjacent to the balloon. These orifices provide a flow path for blood during the angioplasty process. The orifices are designed to provide blood flow while the balloon remains inflated and if, after the balloon is deflated, the blood vessel collapses. However, the device of Sahota still results in insufficient cross sectional flow area in the blood vessel.

It is also desired to provide a balloon catheter which can be used for valvuloplasty procedures. At the present tme, when a valvuloplasty balloon dilatation cathether is inflated across a stenotic heart valve, the heart continues to pump against a completely obstructed valve apparatus, placing severe stress on the heart muscle.

Therefore, it is an object of the present invention to provide a balloon catheter which permits blood flow while the balloon is inflated.

It is a further object of the present invention to provide a balloon catheter which can be kept in place and inflated while the patient is prepared for surgery.

It is still another object of the present invention to provide a balloon catheter which can be utilized for valvuloplasty.

SUMMARY OF THE PRESENT INVENTION

A balloon catheter utilizing a perfusion balloon at one end thereof is described. The perfusion balloon has a donut shaped cross section having a central opening formed therethrough. The central opening provides a blood flow passage even when the balloon is fully inflated. When inflated, the perfusion balloon is used to dilate a stenotic region of a blood vessel or a heart valve to restore blood flow. After deflation, if the blood vessel collapses, the balloon catheter of the present invention can be reinflated and kept in place while the patient is prepared for surgery. In this manner, acceptable blood flow is provided regardless of the length of time required for surgical preparation. In an alternate embodiment, a one-way valve is formed integrally with the perfusion balloon so that the present invention may be applied to valvuloplasty. In this application, the balloon is inflated at a stenotic region of a heart valve to expand the valve and restore acceptable blood fow. The one-way valve of the perfusion balloon takes the place of the heart valve so that normal operation of the heart can be maintained during the valvuloplasty process.

BRIEF DESCRIPTION OF THE DRAWINGS

FIG. 1 is a cross sectional view of a balloon catheter assembly.

FIG. 2 is a side view of an alternate embodiment of the present invention.

FIG. 3a is an end view of the preferred embodiment of the present invention.

FIG. 3b is a cross sectional view of the preferred embodiment of FIG. 3a.

FIG. 3c is a perspective view of the embodiment of FIG. 3a.

FIG. 4a is an end view of an alternate embodiment of the present invention.

FIG. 4b is a cross sectional view of the embodiment of FIG. 4a.

FIG. 4c is a perspective view of the embodiment of FIG. 4a.

DETAILED DESCRIPTION OF THE PRESENT INVENTION

A catheter utilizing a perfusion balloon on one end thereof is described. In the following description numerous specific details, such as catheter diameter, balloon diameter, etc. are set forth in order to provide a more thorough understanding of the present invention. It will be apparent, however, to one skilled in the art, that the present invention may be practiced without these specific details. In other instances, well known features have not been described in detail in order not to unnecessarily obscure the present invention.

The present invention comprises an angioplasty catheter having a perfusion balloon disposed at the distal end for expanding a stenotic blood vessel. The catheter consists of a main lumen, or passage, a minor lumen, a catheter tube and a guide wire. The main lumen permits the passage of a guide wire for steering the catheter into place. The minor lumen provides a fluid path for inflating the perfusion balloon such as with a dye to allow viewing of the stenotic region via x-rays. The perfusion balloon itself is a cylindrical balloon which is substantially donut shaped in cross section. In other words, when inflated, the balloon has a central opening therethrough to permit the flow of blood or other fluids through the blood vessel.

The balloon is a double walled bladder such that when the balloon is inflated, it comprises a hollow shell which in cross section has a central opening therethrough. Prior art balloon catheters having openings in the catheter wall for blood flow around the balloon can leave up to a 92 percent obstruction of the blood vessel cross section. The present invention, even when inflated, provides a passage which is 35 to 60 percent of the original vessel size.

Referring to FIG. 1, a cross sectional view of a typical catheter is illustrated. The catheter assembly consists of a proximal lumen 12 and distal lumen 14. The proximal lumen 12 is a "Y" connector having input ports 21 and 22 and output port 23. Input port 21 includes a central passage 11 for introduction of a guide wire through the catheter assembly. Input port 22 has an opening 13 therethrough which intersects the central opening 11 and is used for the inroduction of medication, if desired, through the catheter.

The distal lumen 14 has ports 24 and 25 and output port 26. The output port 23 of the proximal lumen 12 is coupled to the input port 24 of the distal lumen 14. The distal lumen 14 includes an inner channel 16 therethrough for receiving the guide wire from channel 11 of the proximal lumen. Port 25 includes channel 15 which leads to and surrounds channel 16 and is used for an introduction of inflating fluid and/or radiopaque fluid to the balloon at the catheter tip. Coupled to the output port 26 of the distal lumen 14 is the coaxial catheter assembly consisting of an inner catheter tube 17, an outer "sleeve" catheter tube 28, the balloon 18 and the guide wire 19. The channel 15 between the inner catheter and the sleeve catheter is used for introduction of inflating fluid to the balloon at the catheter tip.

Referring now to distal end 27 of the catheter assembly, the outer sleeve 28 has a constant diameter or may taper to the point of attachment of the balloon 18. The balloon 18 is substantially a widening of the diameter of the outer catheter 28 at the point 29. At point 20, the catheter diameter narrows again. The guide wire 19 exits the balloon and inner catheter at the distal end of the entire catheter assembly.

The balloon of the preferred embodiment of the present invention is illustrated in FIGS. 3a–3c. Referring first to FIG. 3c, a perspective view of the preferred embodiment shows the balloon 36 coupled to one side of the outer sleeve catheter 28. The perfusion balloon of the present invention is essentially a double walled bladder having an outer wall 30 and an inner wall 31. The outer wall 30 connects to the catheter sleeve 28 along line 35. The outer wall continues in a curved path to the inner wall 31. This curved connecting material may be thought of as side wall 34. A gap 33 in the outer catheter 28 provides fluid connection to the interior of the bladder between walls 30 and 31 and to channel 15. When inflating fluid is provides in channel 15, it fills the balloon 36, expanding the balloon into the shape of FIG. 3c.

The perfusion balloon of the present invention, when inflated, takes the shape of an elongated hollow tube. The balloon has a central opening 32 extending coincide with the longitudinal axis of the balloon. This opening 32 has an area which, in the preferred embodiment, is approximately 35–60% of the blood vessel cross sectional area. Referring to FIG. 3a, the cross section of the perfusion balloon is substantially ring shaped, like a doughnut or tire tube. In the preferred embodiment, the perfusion balloon is disposed on one side of the outer catheter 28. However, the outside catheter 28 may be disposed at any orientation and/or or location with respect to the perfusion balloon such as, for example, inside, outside, or in the center.

A typical blood vessel subject to the angioplasty process has a diameter of approximately 2.5 to 3.5 millimeters, resulting in a cross sectional blood flow area of approximately 4.9 to 9.6 square millimeters. The prior art perfusion catheters which provide orifices in the catheter tube for blood flow are limited in cross sectional area to the area of the catheter itself. In other words, when a prior art balloon perfusion catheter is inflated, the only available blood flow path is the catheter tube itself, which is substantially smaller than the blood vessel.

A typical prior art catheter has a diameter of approximately 0.7 mm. Therefore, the cross sectional area of the catheter is 0.38 mm$^2$. This means that at best, only about 8% of the normal cross sectional area is available for blood flow. In other words, the prior art catheter results in a 92% obstruction of the blood vessel when and if the entire cross section of the catheter is available for blood flow. However, some of the cross sectional area of the catheter is taken up by the guide wire, the balloon inflation lumen, and the catheter walls. Therefore, the available cross sectional area generally is less, on the order of 3–4% of the normal blood vessel.

In the preferred embodiment of the present invention, the gap between the inner wall 31 and outer wall 30 of the perfusion balloon, (see FIG. 3a) is approximately 0.5 mm. When inflated, the diameter of the outer wall is coincident with the wall of the blood vessel, or approximately 3 mm. Thus, the diameter of the opening 32 is approximately 2 mm. The cross sectional area of the perfusion balloon available for blood flow is thus 3.14 mm$^2$. The cross sectional area of a 3 mm blood vessel is approximately 7 mm$^2$, so that the present invention provides a blood flow path which is approximately 44% of the maximum available area when inflated. The blood flow area when the balloon is inflated is actually greater than the flow area of a stenotic blood vesse. In a typical stenotic blood vessel, less than 30% of the flow area is available. When the balloon is inflated, approximately half the ideal flow area is available.

For a 3.5 mm blood vessel, assuming a 0.5 mm gap between the inner and outer walls, the perfusion balloon of the present invention provides 4.9 mm² blood flow area. This translates to 51% of the maximum available area of 9.6 mm² in such a blood vessel.

Referring to FIG. 3b, the perfusion balloon 36 is disposed substantially below the outer catheter tube 28. The guide wire 19 extends through inner catheter 17, with channel 16 surrounding the wire for the introduction of fluid to the distal end of the catheter region. The inner catheter 17 is coaxial with outer catheter sleeve 28, with the space between defining channel 15, for introduction of inflating fluid to the balloon 36.

An alternate embodiment of the present invention is illustrated in FIGS. 4a-4c. In this embodiment, the outer catheter 28 is disposed essentially within the circumference of the perfusion balloon 36. Referring to FIG. 4a, the outer wall 30 of the perfusion balloon 36 extends from the walls of the outer catheter 28. Openings 37 and 38 in the side walls of outer catheter 28 provide fluid connection to channel 15 for the introduction of inflating fluid to the balloon 36. As in the previously discussed embodiment, the inner 31 and outer 30 walls of the balloon are connected by side wall 34 to create a double walled bladder. When inflated, the balloon provides an open central passage 32 for the flow of blood in the blood vessel being treated.

Referring now to FIG. 4b, the profile of this embodiment is lower than the profile of the embodiment of FIG. 3b by the approximate circumference of the outer catheter 28. This results in additional blood flow area because the outer catheter is disposed substantially between the inner and outer walls of the balloon 36.

To insure that the spacing between the inner and outer walls of the balloon remains consistent, it may be necessary to provide ribbed members between the walls as spacers. These ribs 39 are shown in FIGS. 4a and 4b and are disposed radially about the center of the balloon. The radial spacing insures complete fluid connectivity to the channel 15 while maintaining the desired 0.5 mm gap between the inner and outer walls of the balloon.

When the catheter assembly is inserted into the blood vessel, it is desired to provide a very low profile so that trauma to vessel walls is minimized. In addition, a low profile may be needed to enable the assembly to be inserted into stenotic regions which have become nearly closed off. The balloon itself is deflated during insertion and positioning of the catheter assembly. In an embodiment of the present invention illustrated in FIG. 2, retaining clips 41 are provided to hold the deflated and folded balloon 36 in place against the outer catheter 28 prior to inflating. The clips 41 are hingedly connected to the outer catheter 28 and "break away" due to the pressure of the balloon when the balloon is inflated. However, although the clips 41 move out away from the balloon 36, they remain attached to the outer catheter 28 so as to be removed from the vessel when the catheter is removed. This perfusion balloon catheter can be similarly used for angioplasty of other arteries of the body.

The present invention may also be utilized for valvuloplasty procedures. If there is a stenosis in one of the heart valves, it is desirable to remove the stenosis or to open up the valve. Generally, the stenosis is such that the valve can close but can only open very slightly. In the past, surgery has been required to correct a valve stenosis. At present, valvuloplasty is being explored as a non-surgical option for correcting these stenoses. If a prior art catheter assembly is utilized, blood flow is cut off completely across the valve, so that the heart is pumping against a completely obstructed outlet, which can lead to damage. This limits the application of prior art catheters to only a few seconds of inflation after which the catheter must be removed. If the balloon can be inflated for longer periods without risk, the valvuloplasty may be more effective.

In an alternate embodiment of the present invention, a one way valve is provided integrally with the perfusion balloon, permitting it to be used in a valvuloplasty procedure. Referring to FIG. 3b, a one way valve 40 is provided within the central passage 32 of the balloon 36. The valve 40 consists of a number of vanes which are coupled at one end to the walls of the passage 32 and curve away from the wall in a downstream direction. When blood is pumped through the valve (from right to left in FIG. 3b) the vanes are urged open, allowing passage of the blood. If blood flows in the other direction, the fluid pressure urges the vanes to come together, preventing flow of blood. It is not necessary that the one way valve be completely fluid tight when off, because even normal heart valves themselves may have some leakage. Further, if the leakage is temporary, no permanent damage results. Thus, the perfusion balloon of the present invention may temporarily take the place of a valve, permitting the use of the present invention in a valvuloplasty procedure.

The perfusion balloon of the present invention is comprised of a flexible plastic material such as polyvinyl chloride (pvc) or any suitable material which can be sterilized for internal applications. The length of the ballon depends on the application but is generally within the range of 2 to 3 cm. for coronary artery angioplasty and 3-6 cm. for valvuloplasty. The diameter of the catheter assembly is approximately 0.3 to 0.8 mm for angioplasty procedures and 2 to 3 mm for valvuloplasty procedures.

As a further alternate embodiment of the present invention, the catheter 28 is disposed within the channel 32 of the balloon. An opening in the catheter 28 communicates with the balloon through inner wall 31 of the balloon. This provides a more rounded cross-section when inflated.

Thus, a perfusion balloon catheter which permits the flow of blood when the balloon is inflated has been described.

I claim:

1. A balloon for use with a catheter assembly comprising:
    a first cylindrical outer wall;
    a second cylindrical inner wall disposed within and coupled to said first outer wall such that a cavity is defined between said first and second walls and an open central passage is defined interiorly of said second wall;
    said first wall having an opening therein for fluid connection to a first channel,
    said first wall being coupled to a first catheter tube,
    said first catheter tube disposed about a second catheter tube, space between said first and second catheter tubes defining said first channel, and wherein said first and second catheter tubes are disposed so as to leave said central passage free of obstructions and permit free flow through said passage.

2. The balloon of claim 1 wherein said first channel is coupled to a fluid source for inflating said balloon.

3. The balloon of claim 1 further including a plurality of ribs coupled to, and disposed between, said first and second walls for defining said cavity between said first and second walls.

4. The balloon of claim 1 further including a one way valve coupled to said balloon for limiting fluid flow in a first direction and permitting fluid flow in a second direction.

5. The invention of claim 1 further including a guide wire extending through said first inner catheter tube.

6. The invention of claim 1 wherein said catheter tubes extend at least partly through said balloon.

7. The invention of claim 6 wherein said catheter tubes extend all the way through said balloon.

8. The invention of claim 1 wherein said first catheter is disposed outward of said inner wall.

9. The invention of claim 8 wherein said second catheter is disposed outward of said inner wall.

10. A catheter assembly comprising:
a first inner catheter coupled to a first lumen;
a guide wire extending through said first inner catheter;
a second outer catheter surrounding and coaxial with said first inner catheter, said second outer catheter coupled to a second lumen;
a balloon coupled to said second catheter, said balloon comprising a first cylindrical outer wall and a second cylindrical inner wall disposed within and coupled to said first outer wall such that a cavity is defined between aid first and second walls and an open central passage is defined interiorly of said second wall, said first outer wall having an opening therein for fluid connection to said second lumen through said second outer catheter;
said second lumen for providing inflating fluid to said balloon through said opening in said first outer wall, and
wherein said first and second catheters are disposed so as to leave said central passage free of obstructions and permit free flow through said passage.

11. The catheter assembly of claim 10 further including a plurality of ribs coupled to, and disposed between, said first and second walls for defining said cavity between said first and second walls.

12. The catheter assembly of claim 10 further including a one way valve coupled to said balloon for limiting fluid flow in a first direction and permitting fluid flow in a second direction.

13. The invention of claim 10 wherein said catheter tubes extend at least partly through said balloon.

14. The invention of claim 13 wherein said catheter tubes extend all the way through said balloon.

15. The invention of claim 10 wherein said first catheter is disposed outward of said inner wall.

16. The invention of claim 15 wherein said second catheter is disposed outward of said inner wall.

17. A method of producing blood flow in a stenotic region of a blood vessel comprising the steps of:
inserting a catheter assembly into said blood vessel, said catheter assembly having a first inner catheter coupled to a first lumen, a guide wire extending through said first inner catheter, and a second outer catheter surrounding and coaxial with said first inner catheter, said second outer catheter coupled to a second lumen;
inflating at said stenotic region a balloon coupled to said second outer catheter to compress said stenotic region, said balloon comprising a first cylindrical outer wall and a second cylindrical inner wall disposed within and coupled to said first outer wall such that a cavity is defined between said first and second walls;
channeling blood flow through said balloon at a flow channel defined within said second cylindrical inner wall when said balloon is inflated, said first and second catheters being disposed so as to leave said flow channel free of obstructions;
whereby blood flow is maintained when said balloon is inflated.

18. The method of claim 17 wherein said said first outer wall of said balloon has an opening formed therein for fluid connection to said second lumen through said second outer catheter.

19. The method of claim 18 wherein said balloon further includes a one way valve coupled to said balloon for limiting fluid flow in a first direction and permitting fluid flow in a second direction.

* * * * *

UNITED STATES PATENT AND TRADEMARK OFFICE
CERTIFICATE OF CORRECTION

PATENT NO. : 4,909,252

DATED : MARCH 20, 1990

INVENTOR(S) : JEFFREY GOLDBERGER

It is certified that error appears in the above-identified patent and that said Letters Patent is hereby corrected as shown below:

Column 7, line 37, in Claim 10: replace "aid" with --said--

Signed and Sealed this

Sixteenth Day of April, 1991

Attest:

Attesting Officer

HARRY F. MANBECK, JR.

Commissioner of Patents and Trademarks